United States Patent

Akao et al.

Patent Number: 5,082,516
Date of Patent: Jan. 21, 1992

[54] PROCESS FOR PRODUCING CHEMICAL ANALYTICAL SLIDE

[75] Inventors: Mutsuo Akao; Takuichi Komatsu, both of Kanagawa, Japan

[73] Assignee: Fuji Photo Film Co., Ltd., Minami-Ashigara, Japan

[21] Appl. No.: 703,594

[22] Filed: May 20, 1991

Related U.S. Application Data

[63] Continuation of Ser. No. 143,393, Jan. 13, 1988, abandoned.

[30] Foreign Application Priority Data

Jan. 13, 1987 [JP] Japan ................................. 62-4048

[51] Int. Cl.$^5$ ............................................. B32B 31/00
[52] U.S. Cl. ................................. 156/277; 422/56; 422/58; 422/102; 422/104; 360/1
[58] Field of Search .............. 422/56, 58, 64, 65, 422/68, 102, 104; 430/307; 101/395, 138; 360/1; 156/625, 626, 636, 637, 654, 660, 905, 277

[56] References Cited

U.S. PATENT DOCUMENTS

| | | | |
|---|---|---|---|
| 4,059,481 | 11/1977 | Nagano | 430/307 |
| 4,169,751 | 10/1979 | Yen | 428/167 |
| 4,323,755 | 4/1982 | Nierenberg | 219/121.61 |
| 4,387,990 | 6/1983 | Yazawa et al. | 422/58 |
| 4,430,299 | 2/1984 | Horne | 422/65 |
| 4,530,286 | 7/1985 | Samuels | 101/395 |
| 4,578,716 | 3/1986 | van Rijckevorsel et al. | 360/1 |
| 4,592,893 | 6/1986 | Poppe et al. | 422/56 |
| 4,719,085 | 1/1988 | Jacobs | 422/56 |
| 4,798,705 | 1/1989 | Jakubowicz et al. | 422/65 |

FOREIGN PATENT DOCUMENTS 57-63452  4/1982  Japan.

Primary Examiner—David L. Lacey
Assistant Examiner—Abanti B. Singla
Attorney, Agent, or Firm—Burns, Doane, Swecker & Mathis

[57] ABSTRACT

A process for producing a chemical analytical slide including an upper slide frame, a lower slide frame and a chemical analytical film therebetween. The process comprises passing a strip sheet in a longitudinal direction, printing a bar code on the strop sheet by intaglio printing so that lines of the bar code extend in the longitudinal direction, forming the upper slide frame or lower slide frame from the printed strip sheet and forming the chemical analytical slide from the printed upper slide frame or lower slide frame. In a further aspect, a chemical analytical slide is provided which has a code which extends from one edge of the slide frame to the opposite edge.

3 Claims, 3 Drawing Sheets

PROCESS FOR PRODUCING CHEMICAL ANALYTICAL SLIDE

This application is a continuation, of application Ser. No. 07/143,393, filed Jan. 13, 1988, now abandoned.

BACKGROUND OF THE INVENTION

1. Field of the Invention

This invention relates to a process for producing a chemical analytical slide having a bar code printed on the surface of the slide frame.

2. Description of the Prior Art

Recently, in the field of clinical tests, dry analysis using a chemical analytical slide has widely been utilized because of the superiorities in the simplicity of analytical operation and rapidity of measurement. In general, the chemical analytical slide is composed of a chemical analytical film containing the reagent reacting with a particular component of a liquid sample such as blood and a slide frame to hold the margin of the chemical analytical slide. On the slide frame, a bar code is printed due to the discrimination of products.

As such a conventional chemical analytical slide, it is known that the chemical analytical film was fixed by a combination of a flat slide frame and the other slide frame having a concavity molded by injection molding (Japanese Patent KOKAI 57-63452). Besides, it is also known that the chemical analytical slide having a hinge similar to a transparent positive film slide, the chemical analytical slide using a paper slide frame (Japanese Utility Model KOKAI 61-116350), and the chemical analytical slide of a cartridge type (Japanese Utility Model KOKAI 54-162294). However, in the case of these chemical analytical slides produced by injection molding, since the bar code was printed on each assembled slide one by one, printing speed was low thereby raising manufacturing cost.

Another chemical analytical slide was developed in order to increase the production speed. The frame of this chemical analytical slide was formed by punching a strip sheet. The chemical analytical slide is, as shown in FIG. 5 and FIG. 6, composed of an upper slide frame 1 and a lower slide frame 2 located at the upper position and the lower position respectively, and a spacer 3 and a chemical analytical slide 4 interposed therebetween. Circular openings 5, 6 are formed near the center of the upper slide frame 1 and the lower slide frame 2, and a bar code 7 is printed on a side portion of the upper slide frame 1. A film hole 8 for placing the chemical analytical film 4 is bored in the center of the spacer 3.

As the method of producing this chemical analytical slide, bar codes were printed on a strip sheet at regular intervals, and the strip sheet was successively punched to produce the upper slide frames 1. The lower frames 2 and the spacers 3 were also produced by punching other strip sheets. The chemical analytical film 4 was inserted into the film hole 8 of the spacer 3, and thereafter, the upper slide frame 1 and the lower slide frame 2 were attached by ultrasonic welding or another method to complete the chemical analytical slide (Japanese Patent KOKAI 61-51570).

However, in the case of the above chemical analytical slide, since the strip sheet was printed with each bar code in a size for each slide frame at regular intervals, it was necessary to be punchased so that the bar code came to a prescribed position. Therefore, the strip sheet should be positioned exactly both in the longitudinal direction and in the lateral direction. Furthermore, the thickness of ink in the latter part of printing was different from the thickness in the beginning causing variations in the ink concentration or the width of the lines of each bar code, or in a particular case, causing a shortage of ink. These brought errors in reading.

SUMMARY OF THE INVENTION

An object of the invention is to provide a process for producing a chemical analytical slide where the slide frame having a bar code is easily and accurately punched.

Another object of the invention is to provide a process capable of producing a chemical analytical slide containing a slide frame having a bar code printed in an uniform ink thickness which does not result in erroneous reading of the bar code.

Still another object of the invention is to provide a process for producing a chemical analytical slide containing a slide frame having a bar code excellent in productivity.

Such objects have been achieved by changing the printed bar code with a bar code arranged in the longitudinal direction of the strip sheet to be punched.

Thus, the present invention provides a process for producing a chemical analytical slide comprising forming an upper slide frame and a lower slide frame by punching strip sheets and attaching the upper slide frame and the lower slide frame on both sides of a chemical analytical film, characterized by that at least one of the strip sheets for forming the upper slide frame and the lower slide frame is printed with a bar code pattern arranged in the longitudinal direction, and thereafter, the printed strip sheet is punched to form the upper slide frame or the lower slide frame.

DETAILED DESCRIPTION OF THE INVENTION

Figure 1:
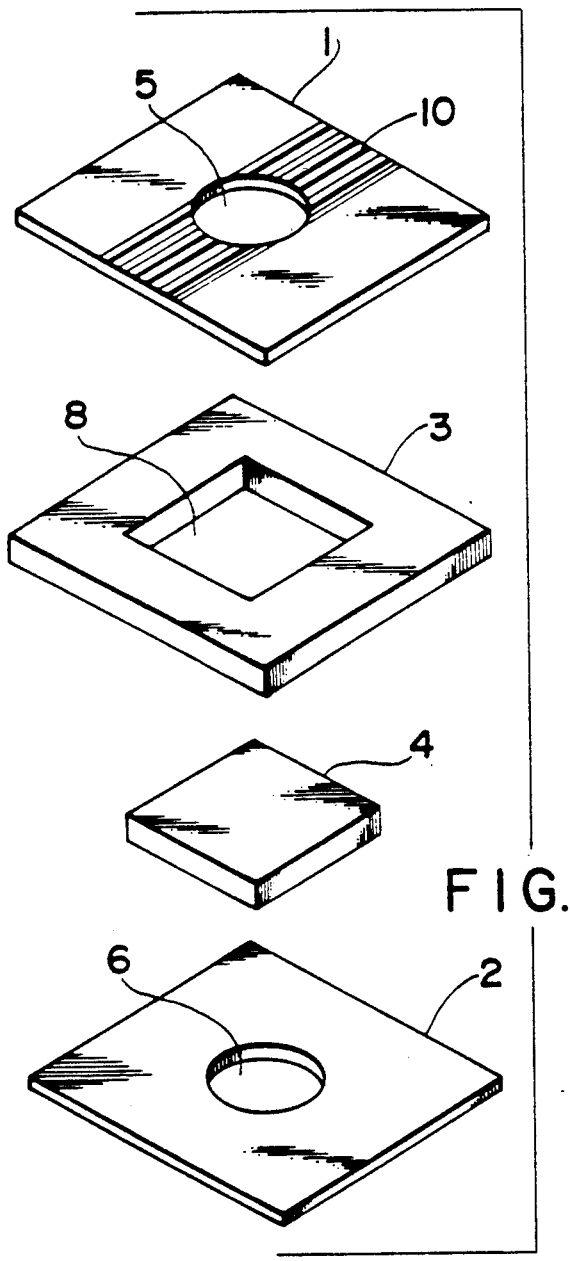
FIG. 1 is an exploded perspective view of a chemical analytical slide produced by the process of the invention.

The strip sheet may be various thermoplastic resin sheets, paper sheets, metal foils or the like. Preferable thermoplastic resin sheets include a polystyrene sheet composed of 90 to 10 wt. % of general purpose (GP) polystyrene and 10 to 90 wt. % of high impact (HI) polystyrene and another polystyrene sheet composed of 99.5 to 85 wt. % of polystyrene and 0.5 to 15 wt. % of various synthetic rubbers. The thermoplastic resin including the above polystyrenes may be blended with various additives such as white pigment or metal powder. Examples of the white pigment are titanium dioxide, calcium carbonate, clay and talc. The thickness of the strip sheet may be sufficient to support a chemical analytical film, and for example, in the case of a polystyrene sheet, it is usually 100 μm to 2 mm.

The bar code pattern may be a single pattern or two or more patterns. In the latter case, the respective pattern may be identical with or different from each other.

The printing process of the bar code pattern may be gravure printing, offset printing or letterpress printing. In the case of gravure printing, the press plate roll may be made by intaglio halftone gravure, helio klischograph method, conventional method or TH process method. In view of printing accuracy, intaglio halftone gravure is particularly preferable. Various printing conditions such as the composition and viscosity of printing ink and printing speed may be varied according to the strip sheet, etc.

The punching process of the upper and lower slide frames and the assembling process may be carried out according to a conventional manner.

The chemical analytical slide may contain other parts such as a spacer interposed between the slide frames.

The kind of the chemical analytical film is not limited, and may be integral multilayer analytical element composed of a transparent support and various layers superposed on it such as spreading layer, reagent layer, registration layer, light-reflecting layer, water absorption layer, binding layer and the like. The component to be analyzed is also not limited, and includes various body fluid components such as glucose, urea, uric acid, cholesterol and the like.

In the process of the invention, since the bar code is made of a continuous line in the longitudinal direction of the strip sheet, precise positioning in the longitudinal direction is not necessary in the punching process. Accordingly, it is enough for the strip sheet to be set in a prescribed position only in the lateral direction. Besides, since the bar code is continuously printed on the strip sheet, the thickness of the printed ink is almost uniform over the whole length of the strip sheet. The ink concentration and the width of the lines of each bar code is also uniform, and the shortage of printed ink does not occur. Therefore, reading errors do not occur. In the case of the process of the invention, productivity is high, and defective products are hardly generated. As a result of these, chemical analytical slides can be produced inexpensively.

EXAMPLES

Figure 2:
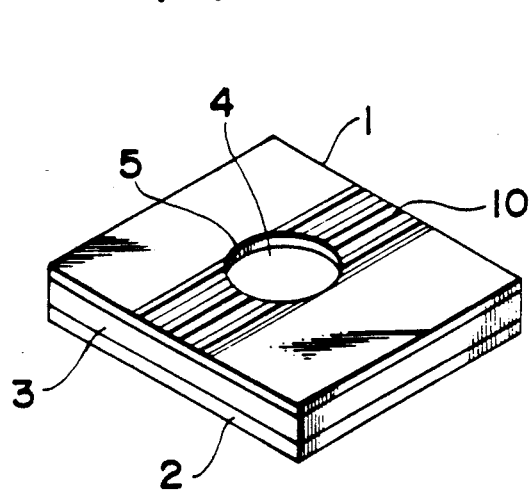
FIG. 2 is a perspective view of the assembled product of the above chemical analytical slide.
Figure 3:
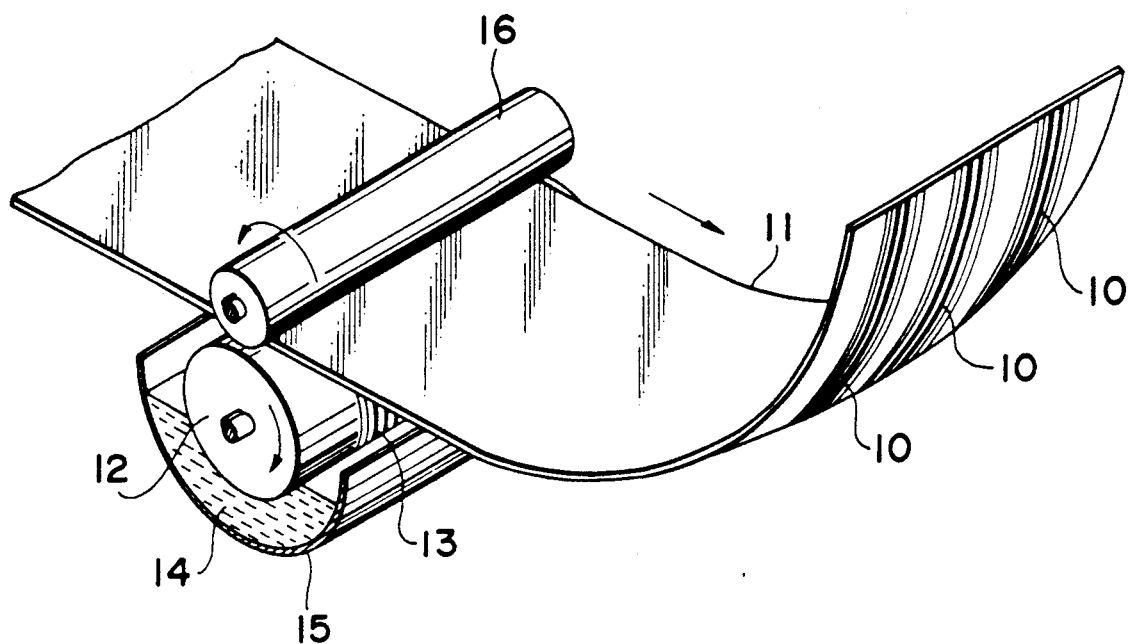
FIG. 3 is a perspective view indicating a printing state of a strip sheet for a slide frame of the chemical analytical slide.

An example of the process of the invention is hereafter explained referring to FIG. 1 to FIG. 3.

Figure 5:
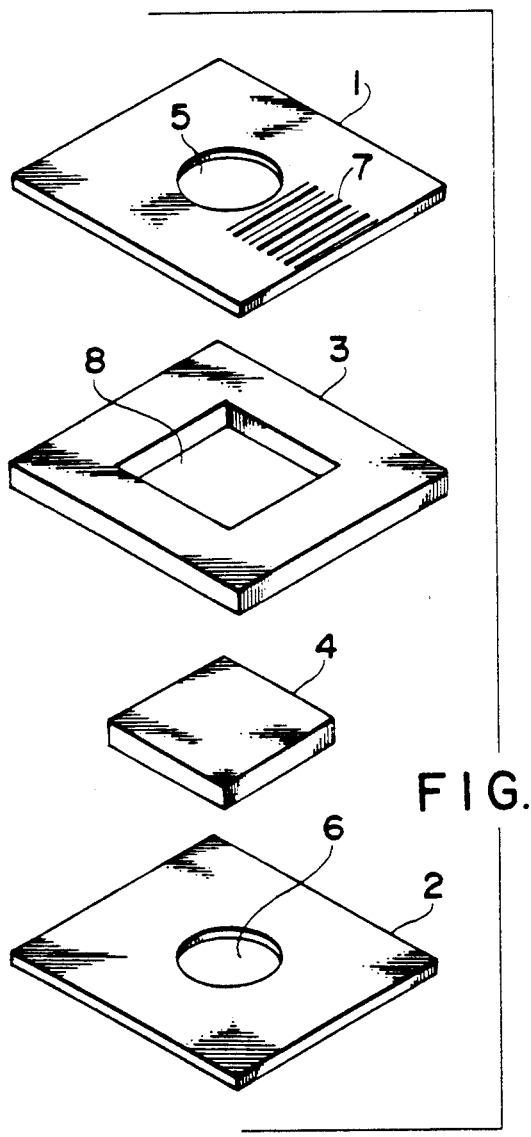
FIG. 5 is an exploded perspective view of a conventional chemical analytical slide.
Figure 6:
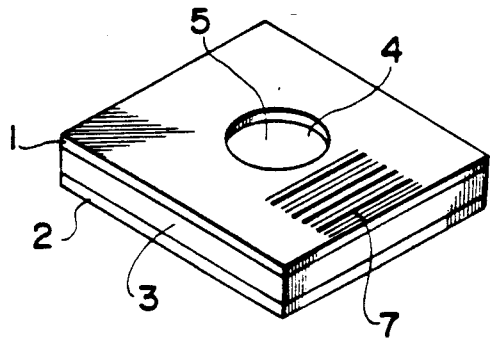
FIG. 6 is a perspective view of the assembled product of the conventional chemical analytical slide.

As illustrated in FIGS. 1 and 2, a bar code 10 is printed on the surface of an upper slide frame in the center extending from one edge to the opposite edge. The remaining parts, i.e. the lower slide frame 2, the spacer 3 and the chemical analytical film 4 are the same as the conventional chemical analytical slide shown in FIGS. 5 and 6.

When the above chemical analytical slide is produced, first, the respective parts are separately prepared. Then, the chemical analytical film 4 is placed on the lower slide frame 2, and the spacer 3 is further placed so that the chemical analytical film 4 is fit in the film hole 8 of the spacer 3. Instead, the spacer 3 may first be placed on the lower slide frame 2, and the chemical analytical film 4 is then placed on the lower slide frame 2. The upper slide frame 1 is placed thereon, and these parts are fixed by means of ultrasonic welding.

The upper slide frame 1 was prepared by punching a strip sheet printed with a bar code pattern composed of continuous lines in the longitudinal direction in a prescribed form. The strip sheet 11 was composed of 70 wt. % of GP polystyrene resin, 28.5 wt. % of HI polystyrene resin and 1.5 wt. % of rutile type $TiO_2$. It was almost flat, and had a thickness of 300 μm. The bar code was printed by gravure printing as shown in FIG. 3. Circular master patterns of the bar code continued in the circumferential direction were formed on the printing face 13 of the press plate roll 12. The printing face 13 was prepared by etching the master patterns of the bar code by means of intaglio halftone gravure into a plate and joining both sides of the plate to form a cylinder. The circumferential length of the press plate roll was 496 mm, and the facial length (printing width) was 380 mm. The ink 14 used was "LOTOSTAR 94 BLACK" (Toyo Ink Mfg. Co., Ltd., Japan), and its viscosity was 16 sec. by Zahn cup #3. The strip sheet 11 was passed between the rotating press plate roll 12 dipped in the ink bath 15 and a pressure roll 16 at a speed of 80 m/min., and thereby, several kinds of bar code patterns 10 were continuously printed on the strip sheet 11 in the longitudinal direction by the printing face 13 of the press plate roll 12.

The strip sheet 11 printed with the bar code patterns 10 were sent to a puncher (not illustrated). Then, the strip sheet 11 was set in a prescribed position in the lateral direction, and punched to form the upper slide frame 1.

The lower slide frame 2 was prepared by punching another strip sheet embossed having the same composition as the aforementioned strip sheet for the upper slide frame 1 and a thickness of 400 μm.

The spacer 3 was prepared by punching another strip sheet embossed having the same composition as the aforementioned strip sheet for the upper slide frame 1 and a thickness of 900 μm.

The chemical analytical film 4 was prepared in a known method, and consisted of a spreading layer, a light-reflecting layer, a reagent layer and a transparent support superposed in this order.

Figure 4:
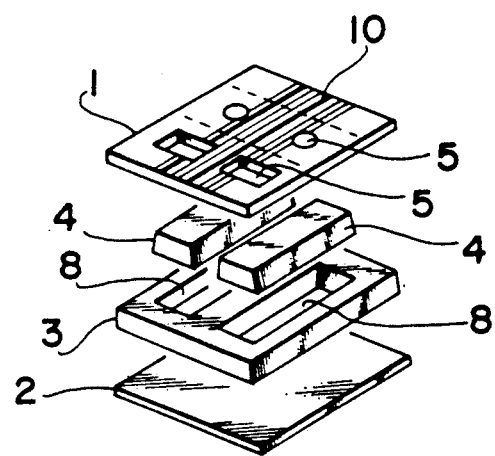
FIG. 4 is an exploded perspective view of another chemical analytical slide produced by the process of the invention.

Another chemical analytical slide produced by the process of the invention is shown in FIG. 4. This chemical analytical slide was an electrolyte type, and also composed of an upper slide frame 1, a lower slide frame 2, a spacer 3 and a chemical analytical slide 4. Each pair of circular openings 5 and square openings 5 were formed in the upper frame 1. The chemical analytical film 4 were composed of two rectangular films, and film holes 8 were bored in the spacer 3 in parallel. The bar code 10 was printed on the surface of the upper slide frame 1 in the center extended from one edge to the opposite edge.

Chemical analytical slides were produced according to three processes embodying the invention and two conventional process, and the results are tabulated in Table.

TABLE 1

| | Invention I | Invention II | Invention III | Conventional I | Conventional II | Test Method |
|---|---|---|---|---|---|---|
| Bar Code Printing Plate | Continuous Roll | Continuous Roll | Continuous Roll | JIS Flat Plate | JIS Roll | |

TABLE 1-continued

|  | Invention I | Invention II | Invention III | Conventional I | Conventional II | Test Method |
|---|---|---|---|---|---|---|
| Engraving | Intaglio Halftone Gravure | Helioklischo-graph *1 | Helioklischo-graph *2 | Intaglio Halftone Gravure | Intaglio Halftone Gravure |  |
| Printing Method | Gravure | Gravure | Gravure | Pad (Dabber) | Gravure |  |
| Upper Slide Frame | Punching Strip Sheet *3 | Punching Strip Sheet *3 | Punching Strip Sheet *3 | Injection Molding | Punching Strip Sheet *3 |  |
| Chemical Analytical Film | For Glucose Analysis | For Glucose Analysis | For Glucose Analysis | For Glucose Analysis | For Glucose Analysis |  |
| Spacer | Punching Strip Sheet *4 | Punching Strip Sheet *4 | Punching Strip Sheet *4 | Injection Molding | Punching Strip Sheet *4 |  |
| Lower Slide Frame | Punching Strip Sheet *5 | Punching Strip Sheet *5 | Punching Strip Sheet *5 | Injection Molding | Punching Strip Sheet *5 |  |
| Printing Speed (sheet/min.) | 2,000 | 2,000 | 2,000 | 12 | 2,000 |  |
| Generation Rate of Defective Product (%) | 0.3 | 3.2 | 1.3 | 13 | 28 | *A |
| Printing Cost Ratio | 8 | 8 | 8 | 100 | 23 | *B |
| Uneveness in Ink Concentration | None | In Some Degree | Rare | In Some Degree | Frequently | *C |

*1 Angle of diamond bit: 130 degrees
*2 Angle of diamond bit: 115 degrees
*3 GP polystyrene resin 70 wt. %
  HI resin 28.5 wt. %
  Rutile type TiO$_2$ 1.5 wt. %
  Thickness 300 μm
*4 The same composition as above
  Thickness 900 μm
*5 The same composition as above
  Thickness 400 μm A $\frac{\text{The number of the slides not read by analyzer}}{\text{Total number of slides}} \times 100$ B Conventional process I is set as 100
C Visual inspection

We claim:

1. A process for producing a chemical analytical slide including an upper slide frame, a lower slide frame with at least one of said upper slide frame and lower slide frame having an opening therein and a chemical analytical film therebetween which is exposed through said opening, said process comprising passing a strip sheet in a longitudinal direction, printing a plurality of bar codes on the strip sheet spaced transversely to the longitudinal direction by intaglio printing so that lines of the bar codes extend in the longitudinal direction, forming a plurality of slide frames from the strip sheet so that a bar code is present on the slide frames, and forming the chemical analytical slide wherein at least one of the upper slide frame and lower slide frame is a slide frame formed from the strip sheet.

2. The process of claim 1 wherein the printing is intaglio halftone gravure.

3. The process of claim 1 wherein the plurality of slide frames are formed by punching the frames from the strip sheet.

* * * * *